United States Patent [19]

Nicoll et al.

[11] Patent Number: 5,196,187

[45] Date of Patent: Mar. 23, 1993

[54] COSMETIC COMPOSITION

[75] Inventors: Gregg A. Nicoll, Dumont, N.J.; Ann C. Ojo-Osagie, Bedford; Mavis C. Pereira, Lower Bebington, both of Great Britain

[73] Assignee: Chesebrough-Pond's USA Co., Division of Conopco, Inc., Greenwich, Conn.

[21] Appl. No.: 698,412

[22] Filed: May 10, 1991

[30] Foreign Application Priority Data

May 10, 1990 [GB] United Kingdom ............... 9010525

[51] Int. Cl.$^5$ ............................................. A61K 7/075
[52] U.S. Cl. ........................................ 424/70; 424/59; 424/63; 514/772.3; 514/844; 514/941
[58] Field of Search .................. 424/70, 63, 59; 514/941, 844, 772.3

[56] References Cited

U.S. PATENT DOCUMENTS

| | | | |
|---|---|---|---|
| 4,105,782 | 8/1978 | Yu et al. | 424/DIG. 4 |
| 4,105,783 | 8/1978 | Yu et al. | 514/459 |
| 4,197,316 | 4/1980 | Yu et al. | 514/554 |
| 4,234,599 | 11/1980 | Van Scott et al. | 514/451 |
| 4,363,815 | 12/1982 | Yu et al. | 514/263 |
| 4,423,041 | 12/1983 | Clum et al. | 514/844 |
| 4,424,234 | 1/1984 | Alderson et al. | 514/558 |
| 4,578,266 | 3/1986 | Tietien et al. | 424/63 |
| 4,801,447 | 1/1989 | Gum | 514/941 |
| 4,871,529 | 10/1989 | Sramek | 424/78 |
| 4,981,845 | 1/1991 | Pereira | 514/941 |
| 5,015,469 | 5/1991 | Yoneyama et al. | 424/63 |
| 5,028,417 | 7/1991 | Bhat et al. | 424/63 |

FOREIGN PATENT DOCUMENTS

| | | |
|---|---|---|
| 0150914 | 8/1985 | European Pat. Off. . |
| 0261812 | 3/1988 | European Pat. Off. . |
| 0271925 | 6/1988 | European Pat. Off. . |
| 2110993 | 9/1972 | Fed. Rep. of Germany . |
| 3824999 | 2/1989 | Fed. Rep. of Germany . |
| 1471679 | 4/1977 | United Kingdom . |
| 2217987 | 11/1989 | United Kingdom . |
| 2217987A | 11/1989 | United Kingdom . |

*Primary Examiner*—Thurman K. Page
*Assistant Examiner*—D. Colucci
*Attorney, Agent, or Firm*—Milton L. Honig

[57] ABSTRACT

A water-pin-silicone oil emulsion, suitable for topical application to mammalian skin or hair, comprises, in addition to water, a volatile polydimethylsiloxane, a silicone surfactant ingredient comprising a polymer of dimethylpolysiloxane with polyoxyethylene and/or polyoxypropylene side chains having a molecular weight of from 10,000 to 50,000, a 2-hydroxyalkanoic acid or derivative thereof, ultrafine titanium dioxide, and an inorganic electrolyte.

13 Claims, No Drawings

COSMETIC COMPOSITION

FIELD OF INVENTION

The invention relates to a water-in-oil emulsion suitable for topical application to human skin and/or hair, to provide enhanced protection from the damaging effects of sunlight. More particularly, the invention is concerned with an exceptionally stable water-in-silicone oil emulsion comprising a hydroxyalkanoic acid and an inorganic sunscreen, which together with the silicone ingredients, provide a product having, in addition to its sunscreen properties, exceptional cosmetic and sensory properties aimed at improving the quality, particularly the plasticity of skin to which it is applied, either as a beauty aid or in the treatment of damaged or diseased skin.

BACKGROUND TO INVENTION & PRIOR ART

A soft, supple and flexible skin has a marked cosmetic appeal and is an attribute of normal functioning epidermis.

As human skin ages with advancing years, the epidermis can become folded or ridged or furrowed to form wrinkles which signal the loss of youthful appearance and herald the transition to old age. This transition can occur prematurely with young people, especially those who expose themselves to excessive doses of sunlight. Also, the outer layer of the epidermis, that is the stratum corneum, can become dry and flaky following exposure to cold weather, or excessive contact with detergents or solvents which result in loss of skin moisture with the result that the skin loses its soft, supple and flexible characteristics.

Emollients such as fats, phospholipids and sterols have in the past been used to soften wrinkled or dry skin, but it is apparent that these emollients are only partially effective as a remedy for skin in poor condition.

The use of 2-hydroxyalkanoic acids for enhancing the quality of human skin following topical application thereto has already been described.

Thus, EP-A 0 007 785 (Unilever) discloses skin treatment compositions incorporating α-hydroxycaproic acid or α-hydroxycaprylic acid or mixtures thereof, the compositions having a pH value of less than 7, usually from 2 to 4.

It is also proposed in U.S. Pat. No. 4,105,782 (Yu & Van Scott) to use amines or ammonium salts of α-hydroxyacids in the treatment of acne or dandruff and, in the Yu & Van Scott patents U.S. Pat. No. 4,105,783 and U.S. Pat. No. 4,197,316, to use such compounds in the treatment of dry skin. U.S. Pat. No. 4,234,599 (Yu & Van Scott) discloses the use of α-hydroxyacids, and their esters or amine salts in the treatment of keratoses. In U.S. Pat. No. 4,363,815 (Yu & Van Scott) it is proposed to use α-hydroxyacids or β-hydroxyacids or keto acids or their derivatives, in a composition for treating skin conditions.

According to GB 1 471 679 (Avon), it is known to use alkali metal salts of $C_2$-$C_5$ α-hydroxycarboxylic acids in moisturising compositions.

In DE 2 110 993 (Henkel), there are disclosed alkali metal salts of $C_4$-$C_{10}$ α-hydroxycarboxylic acids, and the sodium salt of α-hydroxycaprylic acid is mentioned.

In addition to premature ageing of human skin, as seen from the formation of wrinkles, other more immediate damaging effects of sunlight on skin have been observed since time immemorial, such as sunburn (erythema), keratoses and increased incidence of skin cancer (carcinoma), and many remedies have been proposed to protect the skin from this type of damage.

In general terms, harmful ultra-violet radiation, particularly that originating from sunlight, which penetrates the upper atmosphere and reaches the earth's surface, can be classified into:

i. the energy-rich UV-B rays (290-320 nm wavelength) which possess an intense physiopathological activity on the skin; these are absorbed just above the dermis and they are responsible for erythema and skin pigmentation, and ii. UV-A rays (320-400 nm wavelength) which penetrate deeper into the skin (to the dermis and beyond). Their energy is much lower and the photobiological effects they cause are much more long term in nature, for example, they accelerate skin ageing. Certain organic substances (sunscreens) whose molecules absorb the harmful ultra-violet rays have been proposed for use; these substances mitigate the deleterious effects of ultra-violet radiation.

Some of these substances absorb more effectively in UV-A range thereby providing filtering of UV radiation in this range, while others are more effective in the UV-B range.

A common problem exists, however, whatever the choice of organic sunscreen, for protection from whichever wavelength of ultra-violet radiation, and this is that physiological damage to the body can occur, following topical application of these sunscreens in quantities necessary to provide effective filtering of harmful ultra-violet radiation. Even those organic sunscreens that are believed to be safe to use in this way, necessarily have safety limits imposed, based on the quantity applied to the skin, which can result in only moderate to poor protection from harmful ultra-violet radiation.

Certain inorganic substances which physically block ultra-violet exposure of the skin have also been proposed for use as sunscreens. Notable of these is titanium dioxide having a very small particle size. This grade of titanium dioxide, designated ultrafine (also described as micronised) $TiO_2$, affords a good degree of sun blocking potential without the unacceptable skin whitening experienced with the normal pigmentary grade (particle size >300 nm). For example, in DE-A-3824999 (The Boots Company PLC), it is proposed to use titanium dioxide with a mean primary particle size of <100 nm in a water-in-oil emulsion as a sunscreen preparation. This reference also suggests that additional organic sunscreen agents, such as p-aminobenzoic acid and esters thereof, methoxycinnamate, benzophenone, dibenzoylmethanes or salicylates can also be included to improve protection.

In spite of this and other prior proposals, there still exists a need for a completely stable, highly efficient and thoroughly safe sun protection composition which not only provides a wide spectrum of protection in the ultra-violet region, against the aforementioned short and long term damage to the skin that can result from excessive exposure to sunlight, but which can also ameliorate or prevent skin damage following exposure to other adverse climatic conditions or contact with, particularly immersion in detergent solution liable to cause damage. It is with the fulfillment of these needs that the invention is concerned.

SUMMARY OF INVENTION

It is apparent that some emulsions, such as classical oil-in-water emulsions, containing a hydroxyalkanoic acid, such as 2-hydroxyoctanoic acid, suffer from the disadvantage that they lack sufficient stability over long periods of storage at temperatures that may vary from below 0° C. to up to 45° C., that is conditions to which such emulsions can be subjected following manufacture and prior to sale and use by the consumer. This is believed to be due at least partly to the solubilisation of the hydroxyalkanoic acid by the emulsifiers conventionally used in such products, with the consequence that separation of oil and water phases can ensue.

A further consequence of this solubilisation is to release the hydroxyalkanoic acid prematurely from the emulsion, so that its delivery to the skin when the emulsion is applied topically is less efficient and effective. The sensory properties of such emulsions can be poor, due to the presence of the hydroxyalkanoic acid in the continuous phase. This then exerts a dominating influence on the sensory profile, with the consequence that residual stickiness on the skin can be experienced. Also, where protection from the harmful effects of sunlight is required, these emulsions are virtually ineffective unless loaded with one or more organic sunscreens in an amount which can be dangerous to tender skin.

It has now surprisingly been found that a water-in-oil emulsion having the aforementioned desired properties can be obtained by including in it a 2-hydroxyalkanoic acid, a polydimethylcyclosiloxane, a silicone emulsifier ingredient and an inorganic electrolyte, together with an inorganic sunblocking agent, namely ultrafine titanium dioxide.

DEFINITION OF THE INVENTION

Accordingly, the invention provides a water-in-silicone oil emulsion, suitable for topical application to mammalian skin or hair, which comprises, in addition to water;

i. from 1 to 50% by weight of a volatile polydimethylsiloxane, ii. from 0.1 to 25% by weight of a silicone surfactant comprising a polymer of dimethyl polysiloxane with polyoxyethylene and/or polyoxypropylene side chains having a molecular weight of from 10,000 to 50,000 and having the structure:

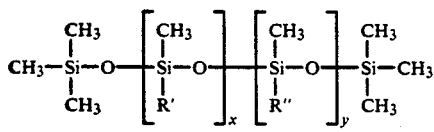

where the groups R' and R" are each chosen from —H, $C_{1-18}$ alkyl and

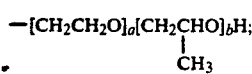

a has a value of from 9 to 115,
b has a value of from 0 to 50,
x has a value of from 133 to 673,
y has a value of from 25 to 0.25, iii. from 0.1 to 10% by weight of a 2-hydroxyalkanoic acid having from 3 to 28 carbon atoms, or a salt, soap, acid-soap thereof, or mixtures thereof;

iv. from 1 to 10% by weight of ultrafine titanium dioxide having an average particle size of from 1 to 100 nm; and v. from 0.001 to 10% by weight of an inorganic electrolyte.

DISCLOSURE OF THE INVENTION

The emulsion of the invention is a water-in-silicone oil emulsion, which is particularly suitable for topical application to mammalian skin or hair, especially that of the human subject, for providing protection from the damaging effects of sunlight. The emulsion is unusual in as much as it is exceptionally stable and retains superior sensory attributes, with a high degree of creaminess, both in terms of feel and appearance, yet without undue whitening, this being due to the careful choice of both a hydroxyalkanoic acid and an inorganic electrolyte, together with a silicone emulsifier and volatile silicone.

The emulsion can also provide a vehicle for other skin and/or hair benefit substances which can thereby be applied, with much greater ease and control to the skin or hair at an appropriate concentration suited to their intended benefit.

The Polydimethylsiloxane

The emulsion of the invention comprises a volatile polydimethylsiloxane such as polydimethylcyclosiloxane having a viscosity of less than 5 $mm^2s^{-1}$, examples of which are DOW CORNING 344 Fluid (tetramer) and DOW CORNING 345 Fluid (pentamer), and volatile hexamethyldisiloxane having a viscosity of not more than 0.65 $mm^2s^{-1}$, for example DOW CORNING 200 Fluid (0.65 $mm^2s^{-1}$).

The preferred volatile siloxane is polydimethylcyclosiloxane (pentamer).

The emulsion will normally comprise from 1 to 50%, preferably from 5 to 20% by weight of the volatile siloxane.

Silicone Surfactant

The emulsion of the invention also comprises a high molecular weight silicone surfactant which acts as an emulsifier.

A preferred silicone surfactant is a high molecular weight polymer of dimethyl polysiloxane with polyoxyethylene and/or polyoxypropylene side chains having a molecular weight of from 10,000 to 50,000 and having the structure:

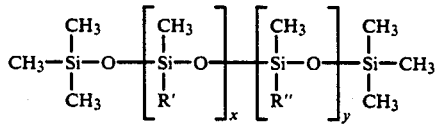

where the groups R' and R" are each chosen from —H, $C_{1-18}$ alkyl and

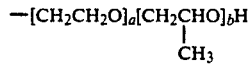

a has a value of from 9 to 115,
b has a value of from 0 to 50, x has a value of from 133 to 673,
y has a value of from 25 to 0.25.

Preferably, the dimethyl polysiloxane polymer is one in which:
a has a value of from 10 to 114
b has a value of from 0 to 49
x has a value of from 388 to 402
y has a value of from 15 to 0.75
one of groups R' and R" being lauryl, and the other having a molecular weight of from 1,000 to 5,000.

A particularly preferred dimethyl polysiloxane polymer is one in which:
a has the value 14
x has the value 249
y has the value 1.25

The dimethyl polysiloxane polymer is conveniently provided as a dispersion in a volatile siloxane, the dispersion comprising, for example, from 1 to 20% by volume of the polymer and from 80 to 99% by volume of the volatile siloxane. Ideally, the dispersion consists of a 10% by volume of the polymer dispersed in the volatile siloxane.

Examples of the volatile siloxanes in which the polysiloxane polymer can be dispersed include those given above.

A particularly preferred silicone surfactant is cyclomethicone and dimethicone copolyol, such as DC 3225C Formulation Aid available from DOW CORNING. Another is laurylmethicone copolyol, such as DC Q2-5200, also available from Dow Corning.

The emulsion according to the invention will normally comprise from 0.1 to 25%, preferably from 0.5 to 15% by weight of the silicone surfactant.

Non-volatile siloxane

The emulsion can also, optionally, comprise a non-volatile siloxane such as a polydimethylsiloxane having a viscosity in excess of 5 mm$^2$s$^{-1}$, for example, from 50 to 1,000 mm$^2$s$^{-1}$, for example DOW CORNING 200 Fluids (standard viscosities 50–1,000 mm$^2$s$^{-1}$).

The Hydroxyalkanoic Acid

The emulsion of the invention also comprises a 2-hydroxyalkanoic acid having from 3 to 28 carbon atoms.

Examples of hydroxyalkanoic acids include:
2-hydroxypropanoic acid
2-hydroxyhexanoic acid
2-hydroxyoctanoic acid
2-hydroxydecanoic acid
2-hydroxydodecanoic acid
2-hydroxytetradecanoic acid
2-hydroxyhexadecanoic acid
2-hydroxyoctadecanoic acid
2-hydroxyeicosanoic acid
2-hydroxydocosanoic acid
2-hydroxytetracosanoic acid
2-hydroxyhexacosanoic acid, and
2-hydroxyoctacosanoic acid Particularly preferred hydroxyalkanoic acids are those having from 3 to 8 carbon atoms, especially
2-hydroxypropanoic acid, and
2-hydroxyoctanoic acid.

The 2-hydroxyalkanoic acids can also be present in the emulsion in the form of their acid-soap complexes having from 6 to 56 carbon atoms, preferred examples of which have an elemental analysis of:

$$(C_m H_{2m-1} O_3)(C_n H_{2n-1} O_3) M$$

where m and n have the same or different values, and each is an integer of from 6 to 28, and M is a cation. The cation M is a monovalent ion such as potassium, sodium, ammonium or a substituted ammonium.

A particularly preferred example of the acid-soap complex is that derived from two molecules of 2-hydroxyoctanoic acid which has the empirical formula $C_{16}H_{31}O_6Na$, as disclosed in EP A O 348 198.

The emulsion according to the invention will normally comprise from 0.1 to 10%, preferably from 0.5 to 5% by weight of the hydroxyalkanoic acid or its acid-soap complex.

The Titanium Dioxide

The emulsion of the invention also comprises as a sunscreen material, ultrafine titanium dioxide having an average particle size of from 1 to 100 nm, preferably from 10 to 40 nm, and most preferably from 15 to 25 nm. Two forms of ultrafine titanium dioxide are available, either or both of which can be employed in the emulsion of the invention, a water-dispersible type and an oil-dispersible type.

Water-dispersible titanium dioxide in accordance with the invention is ultrafine titanium dioxide, the particles of which are uncoated, or coated with a material to impart a hydrophilic surface to the particles. Examples of such materials include aluminium oxide and aluminium silicate.

Oil-dispersible titanium dioxide in accordance with the invention is finely divided titanium dioxide, the particles of which exhibit a hydrophobic surface, and which for this purpose can be coated with metal soaps, such as aluminium stearate, aluminium laurate, zinc stearate, or with organosilicone compounds.

The water-dispersible titanium dioxide, when present, has a greater affinity with the aqueous phase of the emulsion, while the oil-dispersble titanium dioxide, when present, has a greater affinity with the oily phase of the emulsion.

The total amount of titanium dioxide in the emulsion according to the invention is from 1 to 25%, preferably from 1 to 10% by weight of the emulsion. Experimental evidence has shown that emulsions in accordance with the invention which contain less than 1% by weight of ultrafine titanium dioxide, provide little or no protection from excessive exposure to sunlight, while similar emulsions which contain more than 25% by weight of finely divided titanium dioxide do not further improve protection from excessive exposure to sunlight beyond that obtainable when up to 25% of the titanium dioxide is present. Furthermore, an excessive amount of titanium dioxide in the emulsion according to the invention can leave the skin white following topical application of the emulsion.

The protection afforded against the harmful effects of excessive exposure to sunlight by sunscreen materials can be evaluated using an in vitro technique which measures the Sun Protection Factor (SPF) of a sunscreen material itself or a composition containing it (such as the emulsion according to the invention). This technique, which is equally applicable to inorganic sunscreen materials, such as ultrafine titanium dioxide, and organic sunscreen materials, will be described later in this specification.

The Inorganic Electrolyte

The emulsion of the invention also comprises an inorganic electrolyte which serves to improve the stability of the emulsion, particularly when subjected during storage to extremes of temperature.

Examples of inorganic electrolytes include salts, such as alkali metal and ammonium halides, sulphates, nitrates, carbonates and bicarbonates in either anhydrous or hydrated form.

Particularly preferred salts include sodium chloride, potassium chloride and ammonium chloride.

The emulsion according to the invention will normally comprise from 0.1 to 10%, preferably from 0.2 to 5% by weight of an inorganic electrolyte.

Other Ingredients

The emulsion according to the invention can optionally comprise other ingredients, further to enhance its properties and consumer appeal.

Organic Sunscreens

The emulsion of the invention optionally can comprise an organic sunscreen further to enhance the benefit of the emulsion in providing protection from the harmful effects of excessive exposure to sunlight.

As has already been stated, some organic sunscreens can be harmful to health if applied topically to the skin at a concentration sufficient to screen out effectively radiation from either the UV-A range or the UV-B range. The presence however, of ultrafine titanium dioxide, which can provide a broad spectrum of protection, enables a lower than usual amount of organic sunscreen materials to be used to "top-up" the overall Sun Protection Factor of the emulsion to an exceptionally high level, without the risk of causing the type of skin damage or other health problems that can be associated with the use of higher levels of organic sunscreen materials alone.

In view of this, a relatively small amount of organic sunscreen optionally can be incorporated into the emulsion of the invention.

Examples of suitable organic sunscreens, when required, include those set out in Table 1 below, and mixtures thereof.

TABLE 1

| CTFA Name | Trade Name | Supplier |
|---|---|---|
| Benzophenone-3 | UVINUL M-40 | BASF Chemical Co. |
| Benzophenone-4 | UVINUL MS-40 | BASF Chemical Co. |
| Benzophenone-8 | SPECRA-SORB UV-24 | American Cyanamide |
| DEA Methoxycinnamate | BERNEL HYDRO | Bernel Chemical |
| Ethyl dihydroxy-propyl-PABA | AMERSCREEN P | Amerchol Corp. |
| Glyceryl PABA | NIPA G.M.P.A. | Nipa Labs. |
| Homosalate | KEMESTER HMS | Humko Chemical |
| Methyl anthranilate | SUNAROME UVA | Felton Worldwide |
| Octocrylene | UVINUL N-539 | BASF Chemical Co. |
| Octyl dimethyl PABA | AMERSCOL | Amerchol Corp. |
| Octyl methoxy-cinnamate | PARSOL MCX | Bernel Chemical |
| Octyl salicylate | SUNAROME WMO | Fleton Worldwide |
| PABA | PABA | National Starch |
| 2-Phenyl-benzimidazole-5-sulphonic acid | EUSOLEX 232 | EM Industries |
| TEA salicylate | SUNAROME W | Felton Worldwide |
| 3-(4-methylbenzy-lidene)-camphor | EUSOLEX 6300 | EM Industries |
| Benzophenone-1 | UVINUL 400 | BASF Chemical Co. |
| Benzophenone-2 | UVINUL D-50 | BASF Chemical Co. |
| Benzophenone-6 | UVINUL D-49 | BASF Chemical Co. |
| Benzophenone-12 | UVINUL 408 | BASF Chemical Co. |
| 4-Isopropyl dibenzoyl methane | EUSOLEX 8020 | EM Industries |
| Butyl methoxy di-benzoyl methane | PARSOL 1789 | Givaudan Corp. |
| Etocrylene | UVINUL N-35 | BASF Chemical Co. |

The emulsion of the invention can accordingly comprise from 0.1% to 10%, preferably from 1 to 5% by weight of an organic sunscreen material.

Other Inorganic Sunscreens

The emulsion of the invention optionally can comprise an inorganic sunscreen in addition to ultrafine titanium dioxide as herein defined.

Examples of other inorganic sunscreens include:
zinc oxide, having an average particle size of from 1 to 300 nm,
iron oxide, having an average particle size of from 1 to 300 nm,
silica, such as fumed silica, having an average particle size of from 1 to 100 nm.

It should be noted that silica, when used as an ingredient in the emulsion according to the invention can provide protection from infra-red radiation.

The emulsion of the invention can accordingly comprise up to 20%, preferably from 1 to 10% by weight of other inorganic sunscreens.

Alkane Diol

The emulsion of the invention optionally can also comprise an alkane diol, or a mixture thereof, which can serve further to improve and prolong the stability of the emulsion, particularly when a very long period of storage, for example of at least 12 months or even up to 3 years, is anticipated.

The preferred alkane diols for this purpose when used are those having from 2 to 10 carbon atoms in the molecule. Examples of particularly preferred alkane diols are:
ethane diol
propane-1,2-diol
propane-1,3-diol
butane-1,3-diol
butane-1,4-diol
butane-2,3-diol
pentane-1,5-diol
hexane-1,6-diol
octane-1,8-diol, and
decane-1,10-diol An especially preferred alkane diol is butane-1,3-diol.

The emulsion according to the invention can comprise up to 30%, most preferably from 1 to 25% by weight of an alkane diol.

Cosmetically Acceptable Vehicle

The emulsion of the invention optionally can comprise a cosmetically acceptable vehicle, in addition to water, to act as a dilutant, dispersant or carrier for other materials present in the emulsion, so as to facilitate their distribution when the emulsion is applied to the skin and/or hair.

Vehicles other than water can include liquid or solid emollients, solvents, humectants, thickeners and powders. Examples of each of these types of vehicle, which can be used singly or as mixtures of one or more vehicles, are as follows:

Emollients, such as stearyl alcohol, glyceryl monoricinoleate, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, eicosanyl alcohol, behenyl alcohol, cetyl palmitate, di-n-butyl sebacate, isopropyl myristate, isopropyl palmitate, isopropyl stearate, butyl stearate, lanolin, cocoa butter, corn oil, cotton seed oil, olive oil, palm kernel oil, rapeseed oil, safflower seed oil, jojoba oil, evening primrose oil, soybean oil, sunflower seed oil, avocado oil, sesame seed oil, coconut oil, arachis oil, castor oil, acetylated lanolin alcohols, petroleum jelly, mineral oil, butyl myristate, isostearic acid, palmitic acid, isopropyl linoleate, lauryl lactate, myristyl lactate, decyl oleate, myristyl myristate;

Propellants, such as propane, butane, isobutane, dimethyl ether, carbon dioxide, nitrous oxide;

Solvents, such as ethyl alcohol, methylene chloride, isopropanol, acetone, ethylene glycol monoethyl ether, diethylene glycol monobutyl ether, diethylene glycol monoethyl ether, dimethyl sulphoxide, dimethyl formamide, tetrahydrofuran;

Powders, such as chalk, talc, fullers earth, kaolin, starch, gums, colloidal silica sodium polyacrylate, tetra alkyl and/or trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, ethylene glycol monostearate, pigmentary titanium dioxide, titanium dioxide-coated mica.

The cosmetically acceptable vehicle, when present, will usually form up to to 99.9%, preferably from 10 to 99% by weight of the emulsion, and can, in the absence of other cosmetic adjuncts, form the balance of the emulsion.

Cosmetic Adjuncts

Examples of conventional adjuncts which can optionally be employed include preservatives, such as parahydroxy benzoate esters; antioxidants, such as butyl hydroxy toluene; solvents, such as ethyl alcohol and isopropanol; humectants, such as glycerol, sorbitol, 2-pyrrolidone-5-carboxylate, dibutylphthalate, gelatin, polyethylene glycol, preferably PEG 200–600; buffers, such as lactic acid together with a base such as triethanolamine or sodium hydroxide; amino acids such as L-proline waxes, such as beeswax, ozokerite wax, paraffin wax; plant extracts, such as Aloe vera, cornflower, witch hazel, elderflower, cucumber; thickeners; other skin benefit ingredients, such as hyaluronic acid or the sodium salt thereof; activity enhancers; colourants; and perfumes. Cosmetic adjuncts can form up to 50% by weight of the emulsion and can conveniently form the balance of the emulsion.

It is to be explained that the incorporation of L-proline as a cosmetic adjunct into the composition according to the invention is particularly advantageous, as this amino acid is believed to rebuild collagen, a proline-rich protein which is an important structure in skin.

pH

The aqueous phase of the emulsion according to the invention should preferably have a pH value of from 3.5 to <7.

Process for Preparing the Emulsion

The invention also provides a process for the preparation of an emulsion for topical application to skin and/or hair which comprises the step of incorporating into the emulsion a volatile polydimethylsiloxane, a silicone surfactant, a 2-hydroxyalkanoic acid, an inorganic electrolyte and an inorganic sunscreen as herein defined.

Use of the Emulsion

The emulsion according to the invention is intended primarily as a product for topical application to human skin, particularly dry skin, when repeated application can alleviate the dry condition and restore the skin to a more natural, soft, supple, healthy state. The emulsion is also useful for protecting exposed skin from the harmful effects of excessive exposure to sunlight. The emulsion can also be used to treat the hair and the scalp.

In use, a small quantity of the emulsion, for example from 1 to 5 ml, is applied to the affected area of skin or hair, or to exposed areas of skin, from a suitable container or applicator and, if necessary, it is then spread over and/or rubbed into the skin or hair using the hand or fingers or a suitable device.

Product Form and Packaging

The topical skin and/or hair treatment emulsion of the invention can be formulated as a lotion having a viscosity of from 4,000 to 10,000 mPas, a fluid cream having a viscosity of from 10,000 to 20,000 mPas or a cream having a viscosity of from 20,000 to 100,000 mPas, or above. The emulsion can be packaged in a suitable container to suit its viscosity and intended use by the consumer. For example a lotion or a fluid cream can be packaged in a bottle or a roll-ball applicator or a propellant-driven aerosol device or a container fitted with a pump suitable for finger operation. When the emulsion is a cream, it can simply be stored in a nondeformable bottle or squeeze container, such as a tube or a lidded jar.

The invention accordingly also provides a closed container containing a cosmetically acceptable emulsion as herein defined.

Method for determination of Sun Protection Factor (SPF) in vitro

The method for the in vitro SPF determination of the emulsion of the invention involves the spectrophotometric scanning of stratum corneum between 400 nm and 290 nm utilising a Perkin Elmer Lamba 17 spectrophotometer equipped with a diffuse transmission detection system.

Guinea pig stratum corneum is used in place of human skin and the following procedure is followed.

i. Guinea pig stratum corneum is isolated as fine sheets from guinea pig skin and air dried.

ii. A piece of the stratum corneum is applied to the outer surface of a 0.5 cm quartz cuvette using a drop of distilled water to seal the stratum corneum uniformly to the quartz surface.

iii. The quartz cuvette carrying the piece of stratum corneum is placed in the light path of the spectrophotometer which for this purpose is fitted with a fluorescence cut-off filter. This filter eliminates the autofluorescence of the stratum corneum and filters out all transmissions above 400 nm.

iv. The stratum corneum is scanned from 290 to 400 nm and the spectrum obtained is saved as the control.

v. The cuvette with stratum corneum is removed from the spectrophotometer and the test material (i.e. sunscreen) is applied to the stratum corneum at the rate of 1.5 $\mu l/cm^2$, in accordance with German DIN protocol, and rubbed uniformly across the entire surface of the skin using the finger fitted with a finger stall.

vi. The applied sunscreen material is allowed to stand for 5 minutes at room temperature (20° C.) to enable it to dry, and then the sample is rescanned in the spectrophotometer as before from 290 to 400 nm. This spectrum is saved as the test spectrum. No spectral absorbance changes were observed with drying times between 2 and 15 minutes; the 5 minute drying time was therefore adopted as standard.

vii. The control spectrum is subtracted from the test spectrum to provide the spectral absorbance of the test sample of sunscreen material and this absorbance is converted to transmission.

viii. The in vitro Sun Protection Factor (SPF) is finally calculated from transmission measurements as described by Diffey et al in a paper entitled: "A new substrate to measure sunscreen factors throughout the ultraviolet spectrum" in J.Soc. Cosmet. Chem. 40, 127-133 (May/June 1989): see especially page 130.

EXAMPLES

The invention is further illustrated by the following examples.

EXAMPLE 1

This example illustrates a lotion according to the invention.

| Ingredient | % w/w |
|---|---|
| silicone surfactant | 10.00 |
| volatile siloxane | 14.00 |
| mineral oil | 1.50 |
| ultrafine titanium dioxide (water-dispersible) | 5.00 |
| 2-hydroxy octanoic acid | 1.00 |
| 2-hydroxy propanoic acid | 5.00 |
| butylene glycol | 10.00 |
| sodium chloride | 2.00 |
| amino acid | 0.10 |
| neutralising agent | qs |
| preservative | qs |
| perfume | qs |
| water | qs |

Viscosity Data

The viscosity of the above lotion measured on the Brookfield (TB, 10 rpm) was 5,000 mPaS.

Storage Data

The lotion remained stable during storage for 3 months at up to 45° C. and following at least 4 successive freeze-thaw cycles between −22° C. and 20° C.

SPF Data

The lotion when tested in vitro produced an SPF of 7.8 (+/− standard error of the mean (SEM)=0.3).

EXAMPLE 2

This example illustrates a fluid cream according to the invention.

| Ingredient | % w/w |
|---|---|
| volatile siloxane (DC 345) | 8.20 |
| silicone surfactant (DC 3225C) | 12.00 |
| petroleum jelly | 0.50 |
| mineral oil | 1.50 |
| Parsol MCX (octyl methoxycinnamate) | 3.00 |
| ultrafine titanium dioxide (oil-dispersible) | 2.00 |
| sodium chloride | 2.00 |
| butylene glycol | 10.00 |
| l-proline | 0.10 |
| 2-hydroxy octanoic acid | 1.00 |
| 2-hydroxy propanoic acid | 5.00 |
| neutralising agent | qs |
| preservative | qs |
| perfume | qs |
| water | qs |

Viscosity Data

The viscosity of the above fluid cream measured on the Brookfield (TC, 10 rpm) 24 hr after manufacture was 18,600 (mPas).

Storage Data

The fluid cream completed the required three months storage at 45° C. (and 35° C.) as well as four Freeze-/Thaw cycles between −22° C. and 20° C. successfully.

SPF Data

The fluid cream when tested in vitro produced an SPF of 12.6 (+/− SEM=0.5).

EXAMPLE 3

This example illustrates a cream according to the invention.

| Ingredient | % w/w |
|---|---|
| volatile siloxane (DC 345 Fluid) | 8.2 |
| silicone surfactant (DC 3225C) | 12.0 |
| mineral oil | 1.5 |
| petroleum jelly | 0.5 |
| Parsol MCX (octyl methoxycinnamate) | 1.5 |
| ultrafine titanium dioxide (oil-dispersible) | 1.0 |
| 2-hydroxyoctanoic acid | 1.0 |
| 2-hydroxypropanoic acid | 5.0 |
| sodium chloride | 2.0 |
| butylene glycol | 10.0 |
| l-proline | 0.10 |
| neutralising agent | q.s. |
| preservative | q.s. |
| perfume | q.s. |
| water | to 100 |

Viscosity Data

The viscosity of the above cream measured on the Brookfield (TD, 10 rpm) 24 hr after manufacture was 56,000 mPaS.

SPF Data

The cream when tested in vitro produced an SPF of 5.38 (+/− SEM=0.18).

EXAMPLE 4

This example illustrates a lotion according to the invention.

| Ingredient | % w/w |
| --- | --- |
| silicone surfactant (DC 3225C) | 10.00 |
| volatile siloxane (DC 345) | 14.00 |
| mineral oil | 1.50 |
| Parsol MCX | 3.00 |
| ultrafine titanium dioxide (oil-dispersible) | 2.00 |
| butylene glycol | 10.0 |
| sodium chloride | 2.00 |
| l-proline | 0.10 |
| 2-hydroxy octanoic acid | 1.00 |
| 2-hydroxy propanoic acid | 5.00 |
| neutralising agent | qs |
| perfume | qs |
| preservative | qs |
| water | qs |

Viscosity Data

The viscosity of the above lotion measured on the Brookfield (TB, 10 rpm) was 8,000 mPas.

Storage Data

The lotion completed the required storage at 45° C. (and 35° C.) as well as four freeze/thaw cycles between −22° C. and 20° C. successfully.

SPF Data

The lotion when tested in vitro produced an SPF of 9.2 (+/− SEM=0.1).

We claim:

1. A water-in-silicone oil emulsion, suitable for topical application to mammalian skin or hair, which comprises, in addition to water;
   i. from 1 to 50% by weight of a volatile polydimethylsiloxane;
   ii. from 0.1 to 25% by weight of a silicone surfactant;
   iii. from 0.1 to 10% by weight of a 2-hydroxyalkanoic acid having from 3 to 28 carbon atoms, or a salt, soap, acid-soap thereof, or mixtures thereof;
   iv. from 1 to 10% by weight of ultrafine titanium dioxide having an average particle size of from 1 to 100 nm; and
   v. from 0.001 to 10% by weight of an inorganic electrolyte.

2. The emulsion according to claim 1, wherein the silicone surfactant comprises a polymer of dimethyl polysiloxane with polyoxyethylene and/or polyoxypropylene side chains having a molecular weight of from 10,000 to 50,000 and having the structure:

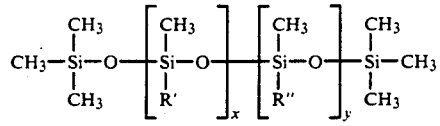

where the groups R' and R" are each chosen from —H, $C_{1-18}$ alkyl and

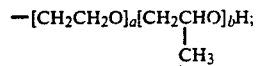

a has a value of from 9 to 115,
b has a value of from 0 to 50,
x has a value of from 133 to 673, and
y has a value of from 25 to 0.25.

3. The emulsion according to claim 1, wherein the 2-hydroxyalkanoic acid is selected from the group consisting of 2-hydroxypropanoic, 2-hydroxyoctanoic acid and mixtures thereof.

4. The emulsion according to claim 1, wherein the ultrafine titanium dioxide is water-dispersible titanium dioxide.

5. The emulsion according to claim 1, wherein the ultrafine titanium dioxide is oil-dispersible titanium dioxide.

6. The emulsion according to claim 1, wherein the inorganic electrolyte is selected from the group consisting of alkali metal and ammonium halides, sulphates, carbonates and mixtures thereof.

7. The emulsion according to claim 1, which further comprises an amino acid.

8. The emulsion according to claim 7, wherein the amino acid is L-proline.

9. The emulsion according to claim 1, which further comprises an alkane diol.

10. The emulsion according to claim 9, wherein the alkane diol is selected from the group consisting of:
    propane-1,2-diol
    propane-1,3-diol
    butane-1,3-diol
    butane-1,4-diol
    butane-2,3-diol
and mixtures thereof.

11. The emulsion according to claim 1, which further comprises an organic sunscreen.

12. The emulsion according to claim 11, wherein the organic sunscreen is octyl methoxycinnamate.

13. A method for protecting human skin from the harmful effects of excessive exposure to ultra-violet rays, which comprise the step of applying to the skin an effective amount of the composition according to claim 1.

* * * * *